US010152582B2

(12) United States Patent
Bolanos et al.

(10) Patent No.: US 10,152,582 B2
(45) Date of Patent: Dec. 11, 2018

(54) SYSTEM AND METHOD FOR SECURING, AND PROVIDING SECURED ACCESS TO ENCRYPTED GLOBAL IDENTITIES EMBEDDED IN A QR CODE

(71) Applicants: Jose Bolanos, Orinda, CA (US); Yanick Gaudet, Cumberland (CA)

(72) Inventors: Jose Bolanos, Orinda, CA (US); Yanick Gaudet, Cumberland (CA)

(*) Notice: Subject to any disclaimer, the term of this patent is extended or adjusted under 35 U.S.C. 154(b) by 694 days.

(21) Appl. No.: 14/665,868

(22) Filed: Mar. 23, 2015

(65) Prior Publication Data

US 2015/0269331 A1 Sep. 24, 2015

Related U.S. Application Data

(60) Provisional application No. 61/967,614, filed on Mar. 24, 2014.

(51) Int. Cl.
| | | |
|---|---|---|
| *G06F 21/34* | (2013.01) | |
| *G06F 21/36* | (2013.01) | |
| *G16H 10/60* | (2018.01) | |
| *G16H 10/65* | (2018.01) | |

(52) U.S. Cl.
CPC .............. *G06F 21/34* (2013.01); *G06F 21/36* (2013.01); *G16H 10/60* (2018.01); *G16H 10/65* (2018.01)

(58) Field of Classification Search
CPC ...................................................... G06F 21/34
See application file for complete search history.

(56) References Cited

U.S. PATENT DOCUMENTS

| | | | | |
|---|---|---|---|---|
| 7,640,579 B2* | 12/2009 | Shewchuk | ............ | H04L 9/3271 713/178 |
| 9,185,095 B1* | 11/2015 | Moritz | .................. | H04L 63/102 |
| 2012/0280049 A1* | 11/2012 | Bennett | .................. | A45C 11/18 235/494 |
| 2013/0167208 A1* | 6/2013 | Shi | .......................... | H04L 63/18 726/5 |
| 2015/0041531 A1* | 2/2015 | Vavala | .................. | A61M 5/172 235/375 |

FOREIGN PATENT DOCUMENTS

WO WO2014082648 * 5/2014 ............ G06Q 30/02

* cited by examiner

*Primary Examiner* — Teshome Hailu
*Assistant Examiner* — Thanh Le (57) ABSTRACT

A computer implemented method for use of encrypted identity on a QR code encoded onto a permanent medium. The system includes mechanism to generate the encrypted identity into a QR code. Also, at patient authentication, the encrypted identity in QR code is read through a custom application. The custom application decrypts the double encrypted global ID using the application encryption key. The server decrypts the application decrypted ID using the server key and date of the encryption. The decrypted global ID is then used to match with the patient information.

13 Claims, 9 Drawing Sheets

SYSTEM AND METHOD FOR SECURING, AND PROVIDING SECURED ACCESS TO ENCRYPTED GLOBAL IDENTITIES EMBEDDED IN A QR CODE

CROSS REFERENCE TO RELATED APPLICATIONS

The present application claims priority from Provisional Patent Application No. 61/967,614 filed on Mar. 24, 2014, which is incorporated herein by reference in their entirety.

BACKGROUND OF THE INVENTION

As the US Government has increased the pressure on hospitals and physicians to advance their healthcare information technologies, problems and deficiencies have been exposed such as: lack of interoperability between Emergency Medical Retrieval (EMR) vendors, Health Information Exchanges (HIEs) and Accountable Care Organizations (ACOs), inaccurate patient record matching, 8-10% national duplicate record rate, and multiple patient identities.

Other key problems include poor authentication mechanisms to access patient health care information used by most insurance carriers and government healthcare agencies. Such authentication mechanisms are often missing multi-factor authentication, using insecure magnetic stripe cards, and/or lacking service validation before payment is rendered. These registration and authentication mechanisms that use insecure magnetic stripe cards lack of multi-factor authentication and/or lacking service validation before payment is rendered. This leaves the door open to fraudulent criminal activity. Multi-factor authentication is now the recommended protocol that is described as: (a) who you are, (b) what you have, and (c) what you know. Internet logins with multiple security questions are of a single-factor authentication type. Multi-factor authentication would include a security token [such as a smart card (microchip)] as what you have and a PIN code as what you know or a picture on the registration system as who you are. Additionally, insecure magnetic stripe credit cards (wherein information is stored in plain text) have led to significant criminal cyber theft including the theft of over 70 million pieces of credit card information. Medicare identity mechanisms for seniors deploy insecure identity cards with only the name and ID on the front of the card. Medicare fraud accounts for over $60-100 billion annually. Most of the Medicare fraud is the result of criminal billing fraud which would have been prevented if proper patient authentication and verification of services was delivered through patient authorization at point of service.

Additionally, any "internal ID" on medical devices such as an SKU, or product ID may be vulnerable to sequence copying. This vulnerability to medical devices has caused significant problems with fraudulent duplication of medical devices, manufactured products, and pharmaceuticals such as pills.

SUMMARY OF THE INVENTION

The disclosure herein addresses these problems using a cloud based software solution that provides a top down enhanced security and work flow solution, centered on a unique security token. Embodiments of the present disclosure may produce a global identifier that may then be double encrypted and embedded into a Quick Response (QR) code. QR code (abbreviated from Quick Response Code) is the trademarked by Denso Wave for a type of matrix barcode (or two-dimensional barcode).

In an embodiment, a patient being registered into a hospital information system, may be assigned a unique identification number (containing 16 digit or more).

In an embodiment, the globally unique identification (global ID) number may then be encrypted twice, once on the server side and once on the client side, using two different encryptions, one using the server key, another using the application key, to create a unique string (which is a string containing 254 digits or more). Once the client side global ID is encrypted, an encrypted QR code will be created and printed on patient's health identity card, mobile app. This encrypted QR code will have a ubiquitous use for insurance cards, hospital wrist bands, and printed medical records.

In one embodiment, patients accessing services through a health care facility may utilize their encrypted QR code identity card to register with the health care system. The encrypted QR code may be read terminal (as described later). Embodiments may run on a mobile device or on Windows or Macintosh computers. An embodiment may take the client side encrypted identifier and decrypts the encrypted QR code using the application key and send the decrypted application identifier to the server. The server machine is a custom cloud based software platform providing access to the patient data and connecting to other hospital information systems. The server may further decrypt the once decrypted application identifier with the server key to access the global ID. This global ID is matched with the patient health record or medical record number that is given to that patient at each healthcare facility. When the facility registers that patient with software platform the server sends the relevant application response back to the software application including the patient record, synchronizing the most accurate demographic, insurance, and emergency medical data for that patient.

BRIEF DESCRIPTION OF THE DRAWINGS

For a more complete understanding of the disclosed subject matter and advantages thereof, reference is now made to the following description taken in conjunction with the accompanying drawings in which like reference numbers indicate like features and wherein.

DETAILED DESCRIPTION

The embodiments disclosed herein are only examples of the many possible advantageous uses and implementations of the innovative teachings presented herein. In general, statements made in the specification of the present application should be interpreted in the broadest form possible. Unless otherwise indicated, singular elements may be in plural and vice versa with no loss of generality.

Exemplary embodiments of the disclosed subject matter are illustrated in the FIGURES, wherein like numerals are used to refer to like and corresponding parts of the various drawings.

This disclosure relates to the use of a cloud base platform to enhance health care patient identity management, using a global identifier which may be double encrypted and processed in to a new QR code that is a new encrypted security token.

An embodiment may generate keys for issuance as health care patient identities to hundreds of millions of users. Embodiments may be tailored to governments, insurance carriers, and hospitals. The disclosed subject matter provides enhanced operational efficiency, decreased costs, improved reimbursements, and increased patient safety. Embodiments of the present disclosure may also be used as a solution for banking and credit card systems at a much lower cost as a replacement for microchip smart cards. Embodiments of the key may be an advanced security token that do not allow for Point of Sale (POS) (Random Access Memory) RAM scraping of credit card information.

A doubly encrypted QR code is created for use with the software application. Only the custom application can make use of the globally unique ID (global ID) encoded in the QR code and make request to the cloud based server with the properly decrypted global ID.

The software system generates a global identifier that is then double encrypted and embedded into a Quick Response (QR) code, this produces an identity management system that protects from "prying eyes" the actual internal ID: (a) insurance ID, (b) hospital medical record number, (c) Physician credentials (d) credit card number, (e) manufacturer ID, (f), product ID, (g) pharmaceutical internal ID, and (h) medical device product ID. QR code (abbreviated from Quick Response Code) is the trademarked by Denso Wave for a type of matrix barcode (or two-dimensional barcode). The security token is an encrypted identifier, which cannot be read by anyone except for custom mobile and desktop applications. A security token may be a physical device that an authorized user of computer services is given to facilitate authentication. The encrypted token is read on the cloud based servers and the patient identity is verified with a Personal Identification Number (PIN) code entered by the patient, allowing for two factor authentication.

The cloud based system communicates with multiple healthcare data EMRs and has that patient's medical record number which prompts the presentation of that facilities' patient record for that patient. The software system includes demographic data, patient image, insurance information, and emergency medical data which will be available to patients to view and correct and will synchronize accurate data across disparate systems, while preventing the creation of duplicate medical records going forward from the time of implementation of the software system. The medical facility will benefit because the correct medical record is found each and every time. Furthermore, by minimizing key strokes the system decreases the likelihood of human error. Having a centralized, enhanced, security identifier for patients will also decrease incidents of patient record duplication, which is a problem that accounts for the 10-12% duplicate medical records throughout the industry. Unnecessary duplication may result in multiple, redundant, patient identities in the health care information systems, which may further faulty data within a patient's medical record. The hospital or provider benefits by having a single accurate record for billing and collections.

The software platform for healthcare has a "Link Engine" that links a generated globally unique ID to other generic IDs such as medical record numbers, health insurance ID, driver's license ID, credit card numbers, and prescription numbers and protects these from fraudulent access and criminal activities.

In the arena of manufacturing of devices, the software platform provides enhanced security of products being manufactured by providing an encrypted security token that is a barrier to viewing product ID and the logistics in sequencing. Each manufactured product in the medical device industry has been mandated by the US Federal government to provide a Universal ID that will be managed by the FDA. This Universal ID is called a UDI or Universal Device Identifier. The encrypted security token will protect that Product ID from fraudulent replication. The software link engine will link the encrypted security token for that product to: (a) manufacturer ID, (b) subcontractor ID, (c) and batch ID. In the pharmaceutical industry, the encrypted security token may be used to register secure containers which will hold a specified quantity of product at either the manufacturer level and when subdivided at the pharmacy level. This system enables the manufacturer to prevent the fraudulent duplication of equipment or drugs. All these products can be verified as authentic by using a smart phone with the customer application to image, decrypt, and verify that the encrypted security token issued is authentic.

Figure 6:
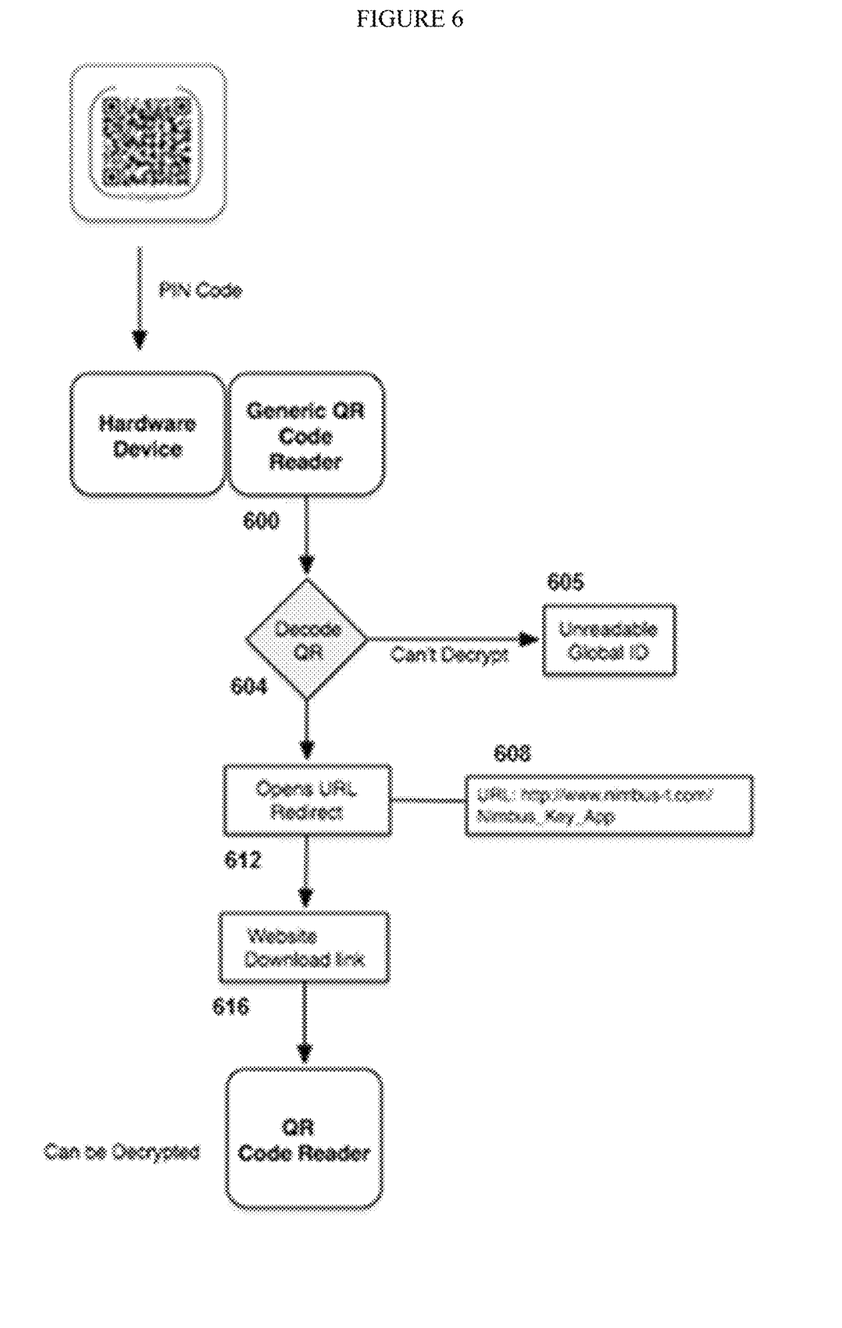
FIG. 6 depicts a work flow diagram when a generic QR code reader application on a mobile device is used to access the encrypted identifier but instead is denied and referred to custom application to register an account.

FIG. 6 shows an exemplary QR code output of the present disclosure. A QR code based encrypted secure identifier is a sophisticated token that enables secure authentication using multi-factor authentication processes.

The present disclosure uses the double encryption mechanism in which the encryption is performed by multiple different keys at separate and distinct parts of the system. Thus, in the present disclosure, the encryption occurs at the mobile application or personal computer terminal level (client side) with its own encryption key, and another encryption occurs at the server level (server side) with its own encryption key.

An encrypted security token is printed on the patient health care card and is used to authenticate patient's identity in the health care information system. The encrypted security token is assisted by multi-factor authentication process. With the use of a PIN code and the patient's picture on the customer cloud software platform, patient's access to information is better secured and generic IDs protected.

QR Code Authentication

When patients need to get services through a health care facility, hospital provider use patient's identity card with secure QR code to access a patient's health care record within the health care system.

Figure 1:
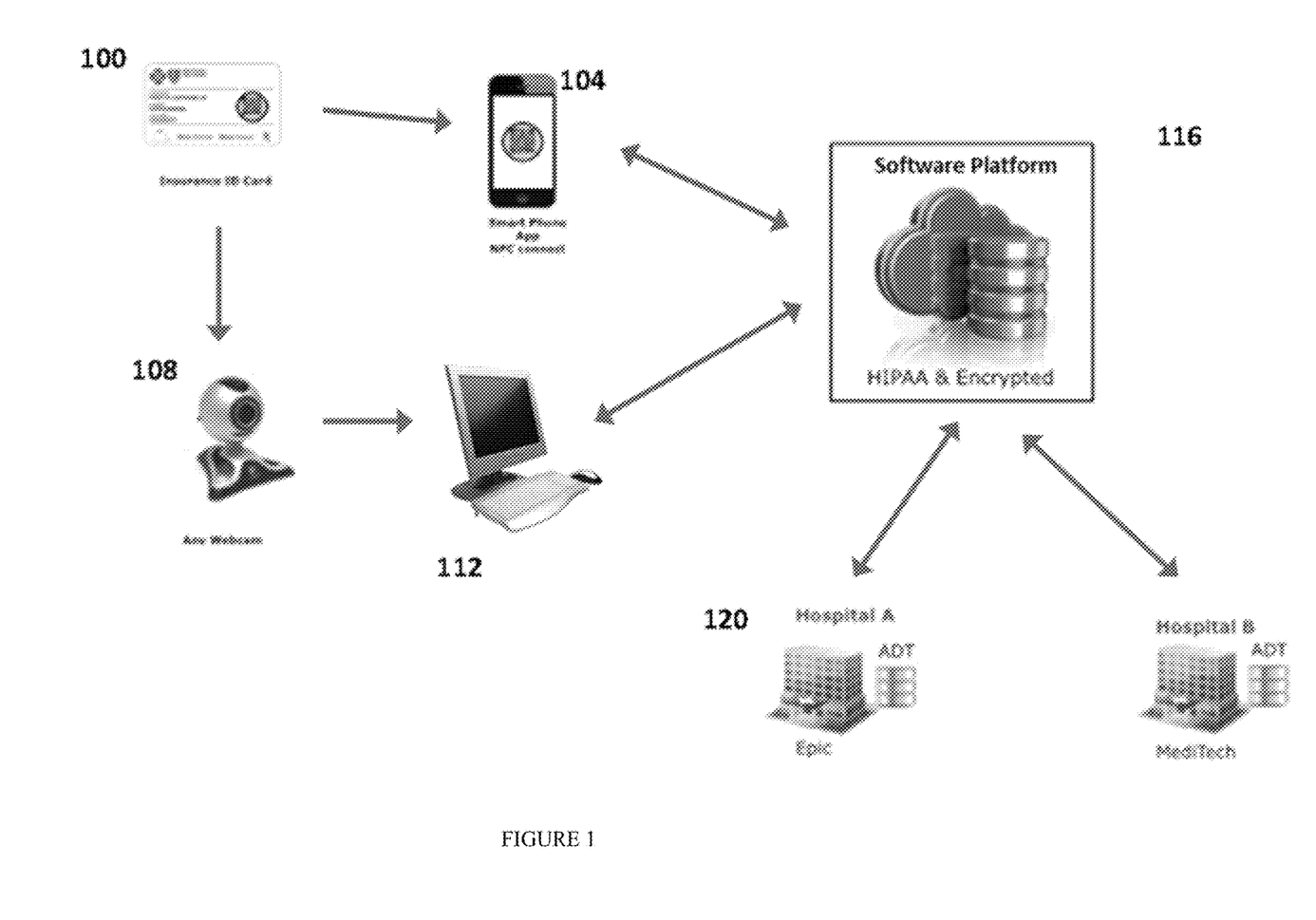
FIG. 1 depicts how the encrypted identifier is decrypted through smart phone, client PC and the server cloud platform as well as linked with other hospital systems.

FIG. 1 shows an embodiment of how the QR code is authenticated using the software platform. When a health care information system tries to identify a patient, the QR code 100 is read through using a webcam 708 on a personal computing device 112, Near Field Communication (NFC) registration Kiosk, or other hospital registration process. The custom application 104,112 first decodes the QR code 700, then the custom software application operating on a mobile phone, or a PC, decrypts the encrypted-secure identifier. Then the customer application passes the encrypted-secure identifier to the cloud software platform 716. The cloud software platform 116 decrypts the encrypted secure identifier to retrieve the global identifier. This global identifier is used to retrieve the patient data and linked to other hospital data 120. All of the patient data is passed back to the mobile device or the PC.

Figure 2:
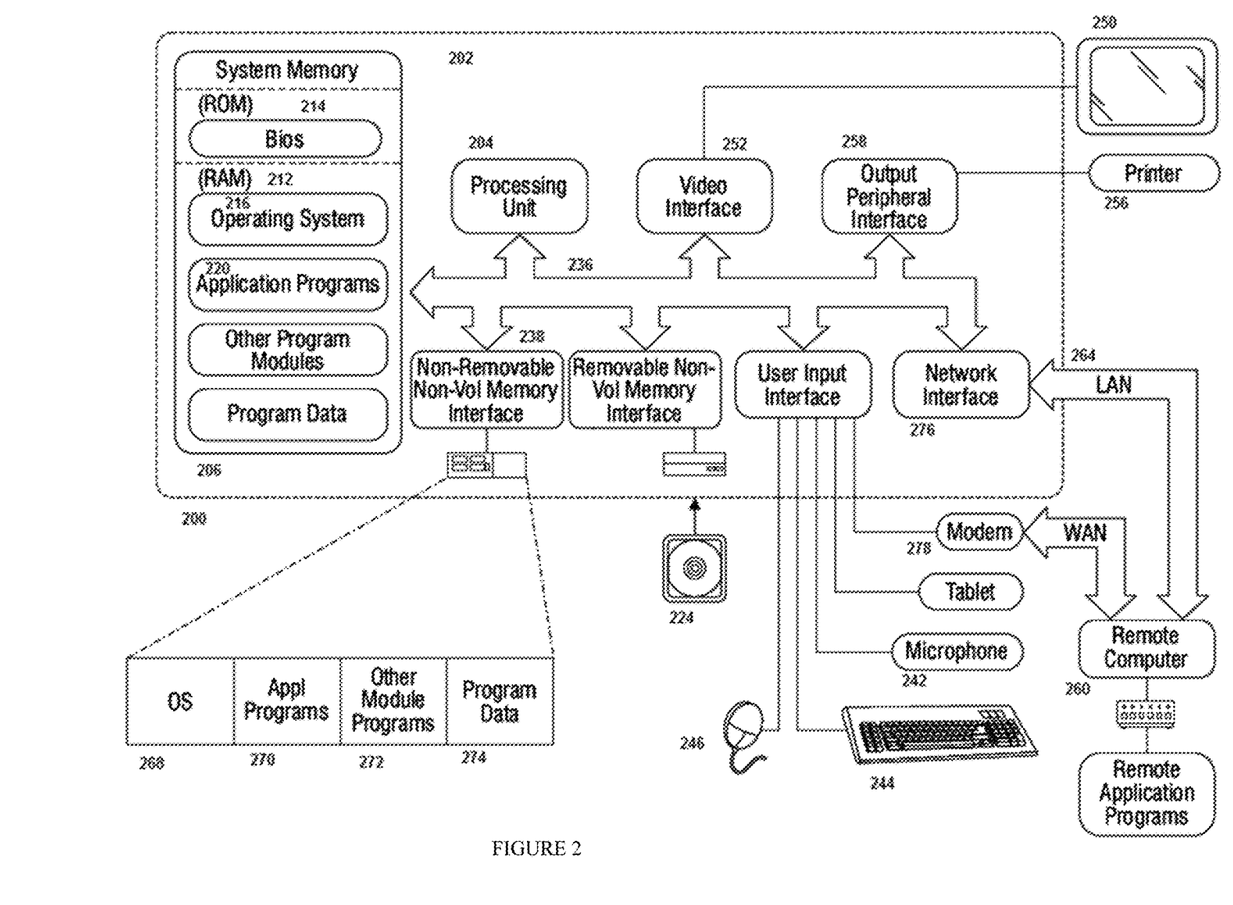
FIG. 2 depicts a computing system being used in the current disclosure.

Illustrated in FIG. 2 is a computing system according to an embodiment of the present disclosure. With reference to FIG. 2, an exemplary system within a computing environment for implementing the invention includes a general purpose computing device in the form of a computing system 200, commercially available from Intel, AMD, and others. Components of the computing system 202 may include, but are not limited to, a processing unit 204, a system memory 206, and a system bus 236 that couples various system components including the system memory to the processing unit 204. The system bus 236 may be any of several types of bus structures including a memory bus or memory controller, a peripheral bus, and a local bus using any of a variety of bus architectures.

Computing system 200 typically includes a variety of computer readable media. Computer readable media can be any available media that can be accessed by the computing system 200 and includes both volatile and nonvolatile media, and removable and non-removable media. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data.

Computer memory includes, but is not limited to, RAM, ROM, EEPROM, flash memory or other memory technology, or any other medium which can be used to store the desired information and which can be accessed by the computing system 200.

The system memory 206 includes computer storage media in the form of volatile and/or nonvolatile memory such as read only memory (ROM) 210 and random access memory (RAM) 212. A basic input/output system 214 (BIOS), containing the basic routines that help to transfer information between elements within computing system 200, such as during start-up, is typically stored in ROM 210. RAM 212 typically contains data and/or program modules that are immediately accessible to and/or presently being operated on by processing unit 204. By way of example, and not limitation, an operating system 216, application programs 220, other program modules 220 and program data 222 are shown.

Computing system 200 may also include other removable/non-removable, volatile/nonvolatile computer storage media. By way of example only, a hard disk drive 224 that reads from or writes to non-removable, nonvolatile magnetic media, or other optical media could be employed to store the invention of the present embodiment. Other removable/non-removable, volatile/nonvolatile computer storage media that can be used in the exemplary operating environment include, but are not limited to, magnetic tape cassettes, flash memory cards, solid state RAM, solid state ROM, and the like. The hard disk drive 224 is typically connected to the system bus 236 through a non-removable memory interface such as interface 234, and are typically connected to the system bus 236 by a removable memory interface, such as interface 238.

The drives and their associated computer storage media, discussed above, provide storage of computer readable instructions, data structures, program modules and other data for the computing system 200. For example, hard disk drive 224 is illustrated as storing operating system 268, application programs 270, other program modules 272 and program data 274. Note that these components can either be the same as or different from operating system 216, application programs 220, other program modules 220, and program data 222. Operating system 268, application programs 270, other program modules 272, and program data 274 are given different numbers hereto illustrates that, at a minimum, they are different copies.

A user may enter commands and information into the computing system 200 through input devices such as a tablet, or a microphone 242, a keyboard 244, pointing device 246, commonly referred to as a mouse, trackball, or touch pad. A user may also enter commands and information into the computing system is through a camera on a smartphone or tablet, and/or QR code reader. These and other input devices are often connected to the processing unit 204 through a user input interface 248 that is coupled to the system bus 208, but may be connected by other interface and bus structures, such as a parallel port, game port or a universal serial bus (USB).

A monitor 250 or other type of display device is also connected to the system bus 208 via an interface, such as a video interface 252. The monitor 250 may also be integrated with a touch-screen panel or the like. Note that the monitor and/or touch screen panel can be physically coupled to a housing in which the computing system 200 is incorporated, such as in a tablet-type personal computer. In addition, computers such as the computing system 200 may also include other peripheral output devices such as printer 256, which may be connected through an output peripheral interface 258 or the like.

Computing system 200 may operate in a networked environment using logical connections to one or more remote computers, such as a remote computing system 260. The remote computing system 260 is a cloud base server services, and typically includes many or all of the elements described above relative to the computing system 200, although only a memory storage device 262 has been illustrated. The logical connections depicted include a local area network (LAN) 264 connecting through network interface 276 and a wide area network (WAN) 266 connecting via modem 278, but may also include other networks. Such networking environments are commonplace in offices, enterprise-wide computer networks, intranets and the Internet.

The central processor operating pursuant to operating system software such as Linux®, UNIX®, Microsoft Windows®, Apple Mac OSX®, Apple iPhone, Android and other commercially available operating systems provides functionality for the services provided by the present invention. The operating system or systems may reside at a central location or distributed locations (i.e., mirrored or stand-alone).

Software programs or modules instruct the operating systems to perform tasks such as, but not limited to, facilitating client requests, security, data storage, and algorithms. The provided functionality may be embodied directly in hardware, in a software module executed by a processor or in any combination of the two.

Furthermore, software operations may be executed, in part or wholly, by one or more servers or a client's system, via hardware, software module or any combination of the two. A software module (program or executable) may reside in RAM memory, flash memory, ROM memory, hard disk, a removable disk, or any other form of storage medium known in the art. An exemplary storage medium is coupled to the processor such that the processor can read information from, and write information to, the storage medium. In the alternative, the storage medium may be integral to the processor. The processor and the storage medium may also reside in an application specific integrated circuit (ASIC). The bus may be an optical or conventional bus operating pursuant to various protocols that are well known in the art.

Data shared and/or used in the various embodiments can also be shared and/or used via a traditional web site or to populate a web site (or other medium). This allows information already assembled in one or more of the other embodiments to be repurposed and thereby raise the value of the disclosed subject matter.

Examples of computing devices such as that depicted in FIG. 2 can include, but are not limited to, portable or mobile devices such as mobile phones (including smartphones), laptop computers, tablet computers, or non-portable devices such as desktop computers, servers, and the like. Such computing devices include, in some examples, various components, such as one or more processors, input devices, communication devices, output devices, storage devices, communications busses, or other components. Each of the components can be interconnected (physically, communicatively, and/or operatively) for inter-component communications. In some examples, the one or more processors of a computing device can execute an operating system that controls operations of components of the computing device, such as by facilitating communication between components of the computing device.

Processors of the computing device, in some examples, are configured to implement functionality and/or process instructions within the computing device. For instance, one or more processors of the computing device can be capable of processing instructions stored in one or more storage devices of the computing device. Examples of such processors can include any one or more of a microprocessor, a controller, or other equivalent discrete or integrated logic circuitry.

One or more storage devices of a computing device can be configured to store information within the computing device during operation. Such storage devices can be described as computer-readable storage media. In some examples, a computer-readable storage medium can include a non-transitory medium. The term "non-transitory" can indicate that the storage medium is not embodied in a carrier wave or a propagated signal. In certain examples, a non-transitory storage medium can store data that can, over time, change (e.g., in RAM or cache). In some examples, a storage device can be a temporary memory, meaning that a primary purpose of the storage device is not long-term storage. Storage devices, in some examples, can be described as volatile memory, meaning that the storage device does not maintain stored contents when power to the computing device is turned off. Examples of volatile memories can include random access memories (RAM), dynamic random access memories (DRAM), static random access memories (SRAM), and other forms of volatile memories. In some examples, a storage device can be used to store program instructions for execution by one or more processors. Storage devices, in certain examples, can be used by software or applications running on the computing device to temporarily store information during program execution.

Storage devices, in some examples, also include one or more computer-readable storage media. Storage devices can be configured to store larger amounts of information than volatile memory. Storage devices can further be configured for long-term storage of information. In some examples, storage devices can include non-volatile storage elements. Elements of such non-volatile storage elements can include magnetic hard discs, optical discs, or flash memories.

A computing device can, in some examples, include one or more communication devices. For instance, a computing device can utilize a communication device to communicate with external devices via one or more networks, such as wired or wireless networks or both. A communication device can be a network interface card, such as an Ethernet card, an optical transceiver, a radio frequency transceiver, or any other type of device that can send and receive information. Other examples of such network interfaces can include, but are not limited to, Bluetooth, 3G, 4G, WiFi radio computing devices, as well as Universal Serial Bus (USB).

In certain examples, a computing device can utilize a communications device to communicate with one or more external devices via a communications network. In some examples, components of Platform can be distributed among multiple computing devices, which can be interconnected via the communications network. Examples of such a communications network can include one or more wired or wireless networks or both, such as local area networks (LANs), wireless local area networks (WLANs), cellular networks, wide area networks (WANs) such as the Internet, or other types of networks.

A computing device can also include one or more input devices and/or output devices. An input device, in some examples, can be configured to receive input from a user. Examples of input devices can include any one or more of a mouse, a keyboard, a microphone, a camera device, QR code reader, a presence-sensitive and/or touch-sensitive display, or other type of device configured to receive input from a user. Output devices can be configured to provide output to a user. Examples of output devices can include a display device, a sound card, a video graphics card, a speaker, a cathode ray tube (CRT) monitor, a liquid crystal display (LCD) an organic light emitting diode (OLED) display, or other type of device for outputting information.

Figure 3:
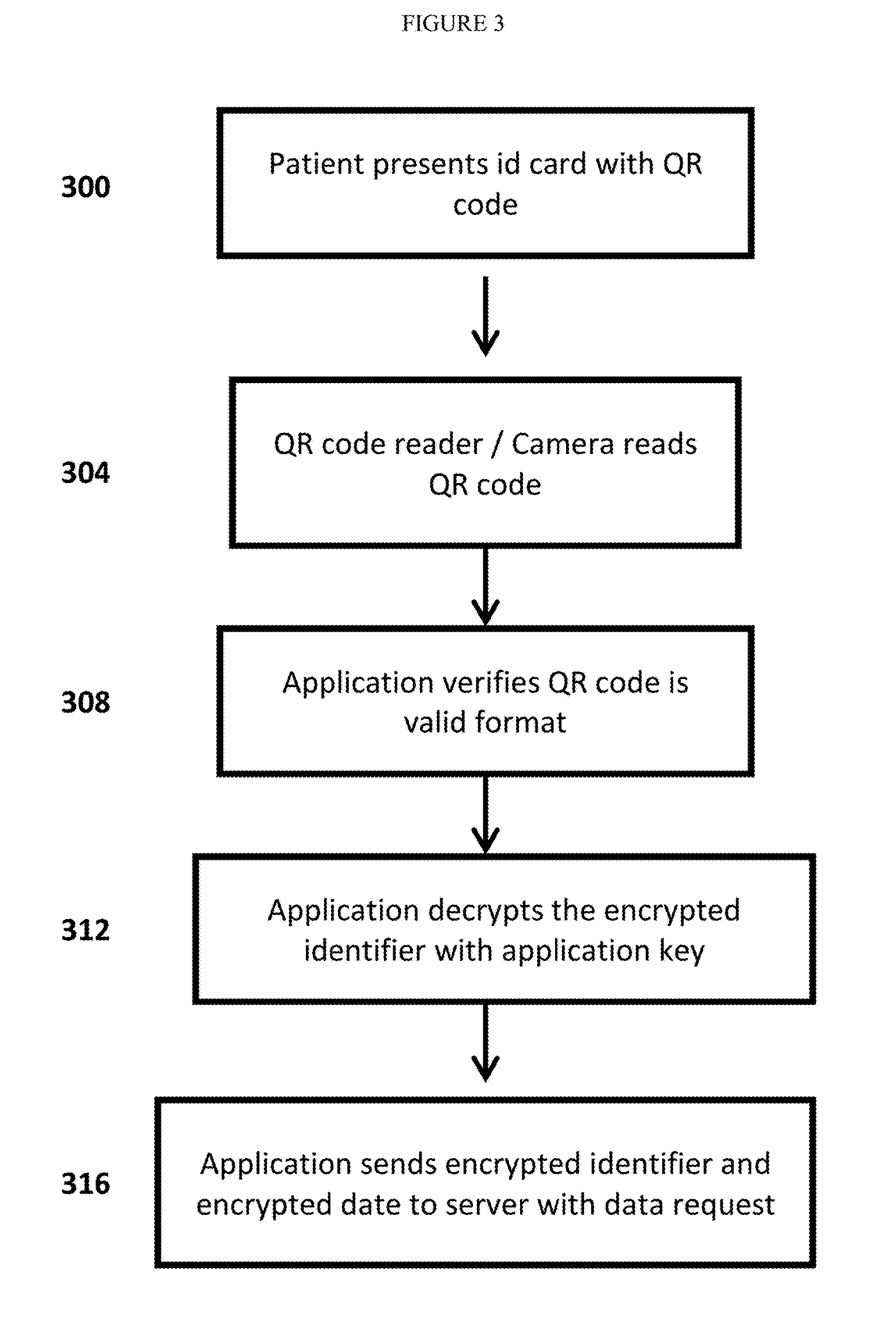
FIG. 3 depicts the decryption process from the patient and client application perspective such as mobile phone or QR code reader attached to a PC.

FIG. 3 shows another depiction how the QR code is read through a QR reader or smart phone and processed through the software platform from the client application perspective. When a health care information system tries to identify a patient, the QR code 300 is read through the custom software application using a webcam 304 on a personal computing device 304, Near Field Communication (NFC) registration Kiosk, or other hospital registration process. Similar process can be applied to identifying a generic ID, medical device, or pharmaceutical pill. The custom application 312 first decodes the QR code 300, then the custom software application checks to see if the QR code has been created by the software platform so as to not create duplicate records. If the QR code is authenticated as being previously generated by the software platform, the software application decrypts the double encrypted global ID using the application encryption key 312 into an application decrypted ID. The software application will also extract out the validation date when the encryption took place. The format of the decoded QR code is: http://www.website.com?id=[encrypted identifier string].

The client application will post the patient information request to the server using its representational state transfer (REST) services, passing the application decrypted ID, the date of the encryption and other application information (i.e. MAC address, geo-location and the user information) 316. The client application post requests to the server through a Secure Sockets Layer (SSL) encrypted service port. Only requests made using the above specified information will return patient information.

FIG. 6 shows the process when the system determines that the QR code was not generated by the software system. If the software application is unable to decrypt double encrypted ID embedded in the QR code using the application key, then the QR code is determined to be not generated by the software platform 205. If the software application determines that the QR code is not generated from the software platform, then the software application opens the URL 212 of the website to sign up for the software platform, the patient registers to get a security token, mobile application, and a generated identity card.

The client application caches the double encrypted ID for the duration of the session for other requests from the client application. The application decrypted global ID is not stored on the software application and is decrypted every time the patient information is requested.

Figure 4:
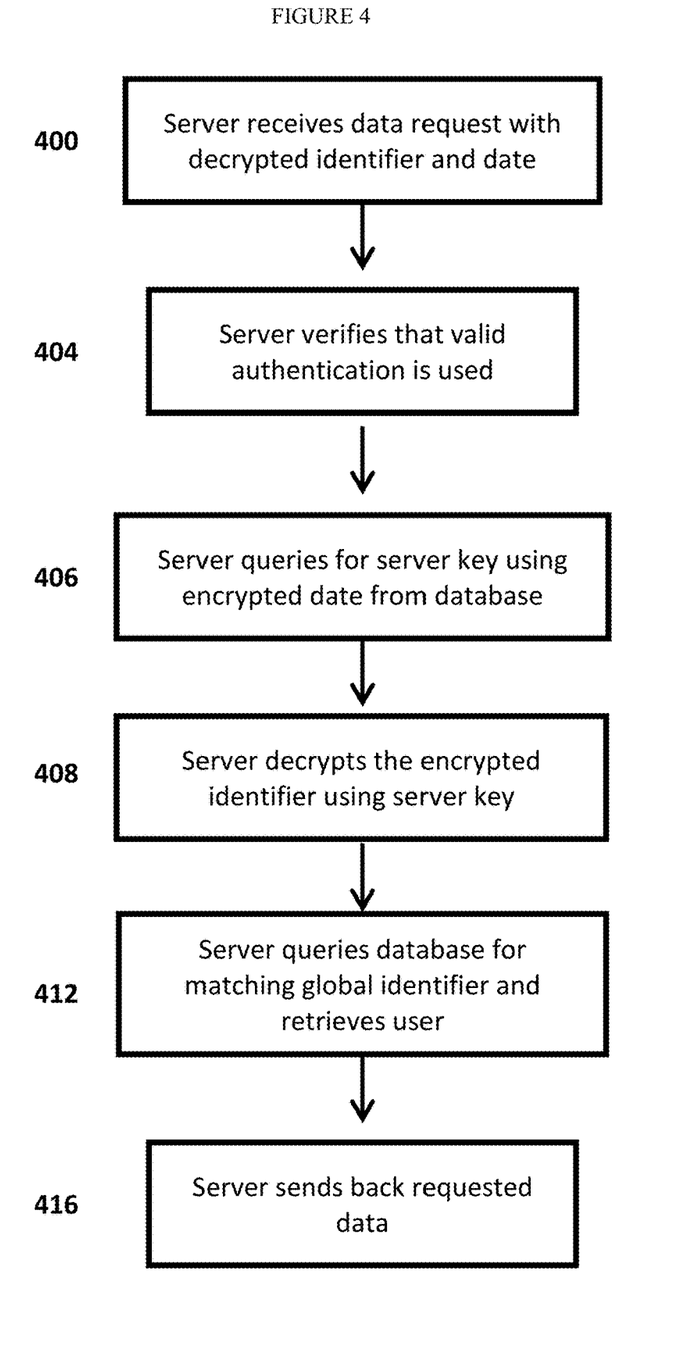
FIG. 4 depicts the decryption process from cloud server perspectives.

FIG. 4 shows how the server decrypts the encrypted identifier. The server is configured to receive and respond only to requests coming from the client software applications or widgets, created and published using the custom software platform. When a request is received by the server 400, the server checks to see if the sending application is a valid user in the software platform 404. If that user validates, the server uses the encryption date of the encrypted security token to look up the known valid date ranges for the server keys 406. The encryption date might not match any of the valid date ranges because the administrator of the software platform has detected security fraud and determined that the security of one of the server keys has been compromised and has remove the server key from the list of valid server keys. The fraud detection mechanism is outside the scope of this patent. If the date does not match any known validate date ranges for server keys, the server stops processing the request and sends error notice/response to the custom application.

Once the server key is found, the server tries to decrypt the encrypted ID. The application decrypted ID (client decryption) is analyzed and decrypted 408 using the server key (server decryption) and date of the encryption. If the server decryption process fails to decrypt the encrypted ID into a valid global ID, the server stops the processing of the request and sends an error notice/response to the software application. The application decrypted identifier is not stored or cached on the server.

The global identifier is then used to match with the patient information 412. Once the patient record has been matched by the above process, the requested patient information is then sent back to the client application and the facility's Admit-Discharge Transfer (ADT) system is activated and the software platform requests the patient's medical record through Health Level 7 (HL7) communication.

Figure 5:
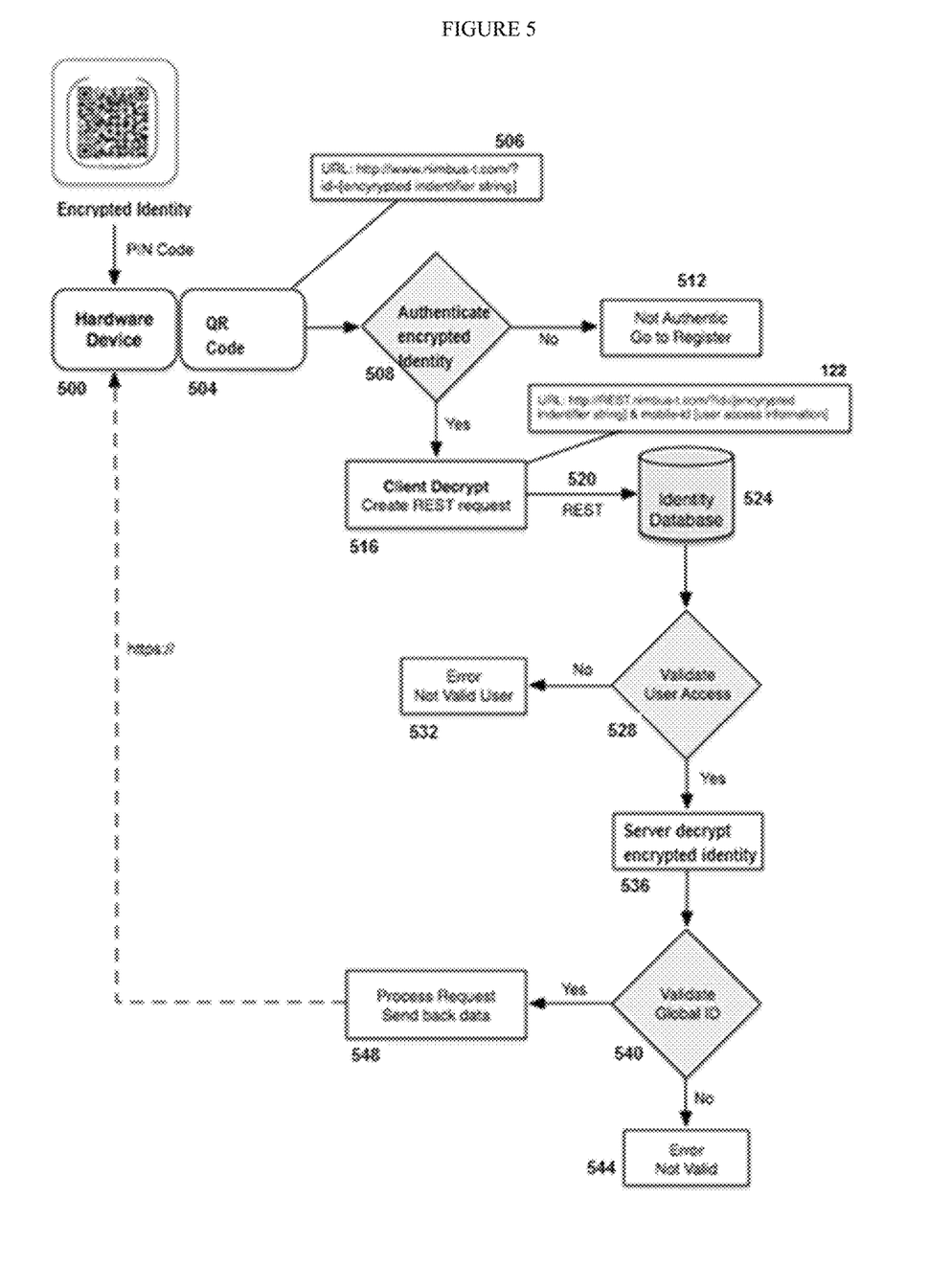
FIG. 5 depicts a work flow diagram illustrating how the present disclosure may be used to verify the authenticity of a health care patient.

FIG. 5 shows an embodiment in which the smartphone and/or PC interaction is combined with a cloud based server interactions.

FIG. 6 shows another embodiment in which the work flow of when the encrypted security token is read using the generic QR code reader 600 rather than using the custom application to read the encrypted security token. The generic QR code reader would decode the QR code 604 in the format 608: http://www.website.com?id=[encrypted identifier string]. The generic QR code reader would then navigate to the website 612 using the above URL and would encounter an error page stating that the encrypted security token can only be read by a custom client application. The website would display a button to download the software application for either mobile or personal computer 616.

Figure 7:
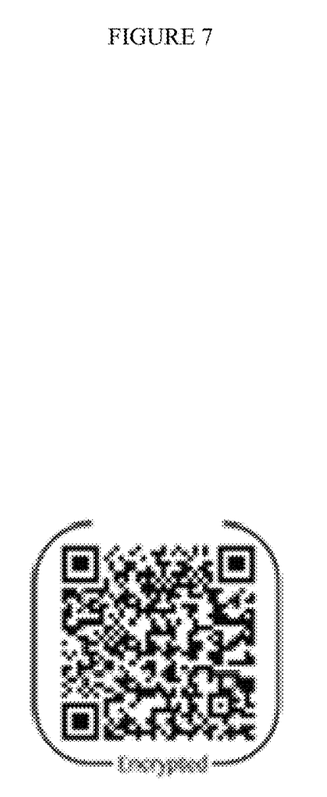
FIG. 7 depicts an example of the QR code generated using an embodiment.

FIG. 7 shows an embodiment of the key, a double encrypted QR code, generated by the software platform.

Identity Key Generation for Patients and Healthcare

The encrypted security token is the focal identification component that will authenticate and allow secure interaction with the software platform. The concept behind encrypted security token is to provide an easily readable form of identity code to identify and link to specific patient health information record. The encoded QR code includes general availability information, the web address of QR generated key, and proprietary information including the encrypted patient identifier.

Figure 8:
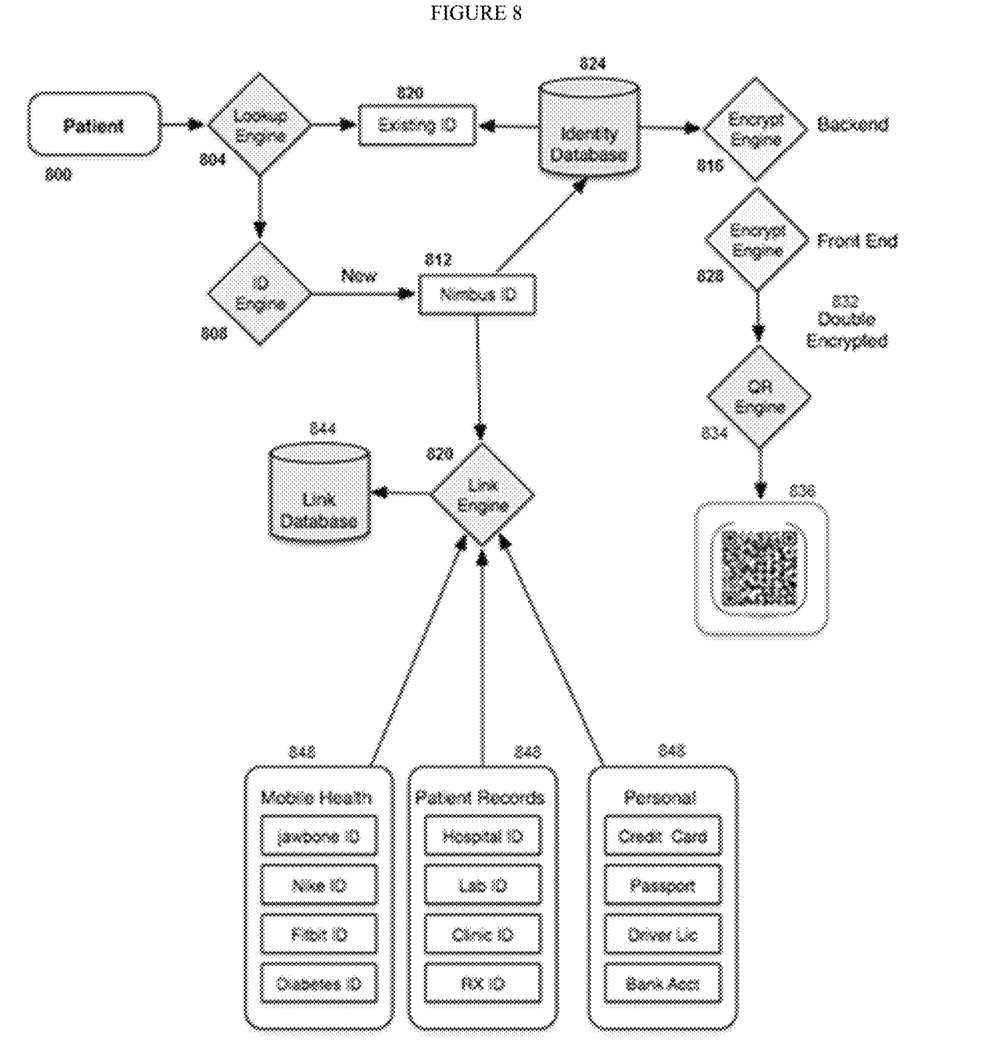
FIG. 8 depicts a work flow diagram illustrating a security token generation schema for healthcare and personal identity protection.
Figure 9:
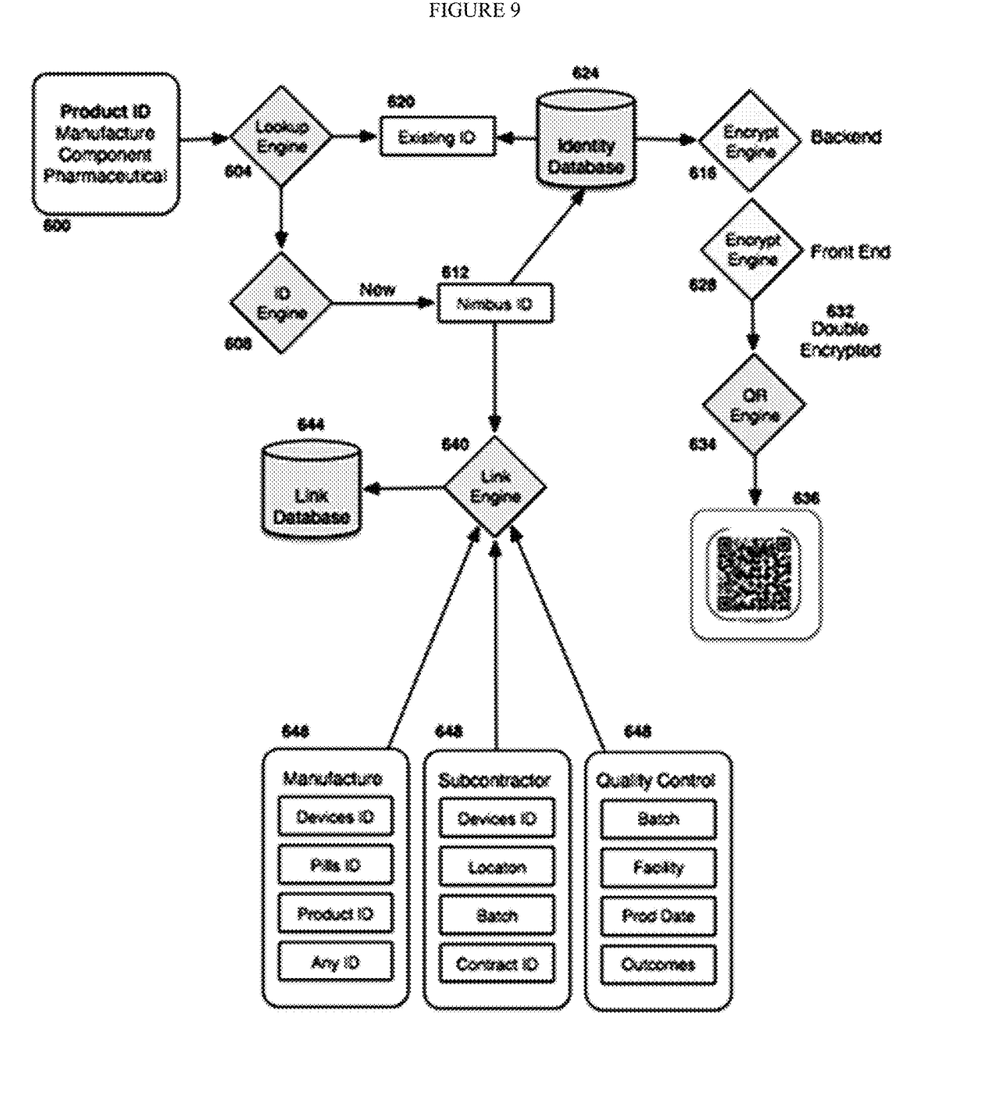
FIG. 9 depicts a work flow diagram illustrating a security token generation schema for manufacturer and product ID protection.

FIG. 8 illustrates how a patient registers within the hospital information system to generate an encrypted security token via the software platform. Similar process is used for registered a generic ID, a medical device, a pharmaceutical pill or a credit card (FIG. 9). When a patient 800, a product ID or manufactured component 900 is registered into a health care information system, the software platform checks to see if the patient, a product ID or manufactured component 900 has already been registered within the system using the lookup engine 804, 904. If person already is registered with the system 820, 920 then the existing globally unique ID (global ID) is assigned. If the patient does not exist in the system, software platform using the ID engine 808, 908 generates a new unique ID 812, 912 (containing 16 digits or more) assigns the newly generated ID to the new patient, and stores the newly assigned global ID in the database 824, 924. For example, the ID can be: 5269adfe5b741aa39fae4284.

The software platform then uses the encryption engine 816 to encrypt the global ID with a server key, creating the server encrypted ID. The encryption process is achieved by passing the global ID through the application programming interface (API) of an encryption algorithm. Encryption algorithm implementation is not limited to any specific algorithms but can use any well-known encryption algorithms such as 3DES, ARCFOUR, BLOWFISH, CAST_256, CRYPT, DES, DES_COMPAT, ENIGMA, GOST, IDEA, LOKI97, MARS, PANAMA, RIJNDAEL, RC6_256, SAFER64, SAFER128, SAFERPLUS, SERPENT, SKIPJACK, TEAN, THREEWAY, TRIPLEDES, TWOFISH, WAKE, XTEA, etc.

In order to enhance the security of the encrypted security token, the server key is valid for limited duration of time. That duration can be as little as two weeks or as long as six months. Limiting when the server key is valid minimizes the number of physical cards with secured QR code exposed to security intrusion if a server key is compromised. If the security of a server key has been compromised, all the cards associated with the server key are re-issued to the patients. If an expired encrypted QR code is used to access the software platform, the encrypted date stored on the QR code would not find any valid date ranges for the server keys and the system reject the authorization of the encrypted QR code.

The server keys and the valid date ranges are stored in a repository separate from the patient database. In this example, the server encrypted global ID may be:

U2FsdGVkX190Dh8fV0mlyAu+6WW+ rPCZ6y0m64ifJmoabAqokniDQQ0Ni1S1AJ9/

The server encrypted global ID is then encrypted 828 using the application key through the encryption engine, creating the doubly encrypted global ID 832, 932 (containing 254 digits or more). The date that the server key was encrypted is embedded in the double encrypted global ID. The application key is stored in the software application on a mobile device, or a personal computer. The mobile application may run on Apple iOS (for iPhone or iPad), Android systems, on any other mobile devices, or on Windows or Macintosh PCs. In our example, the doubly encrypted id 832, 932 is now:

U2FsdGVkX18ACGX1WK75GN5Idhgzp8Ajw/ qZJtnHk8dnEKH9DL4QcJs JtyThyK6QzDerhaNGeabn6nPoym9kFU2TZ2f4ke6Q-ktelNe4/Cr10kcZFZWbDYJR MuWODad9o. (The encrypted code is never stored with the patient record)

This double encrypted ID is then added to the end of a web site Uniform Resource Locator (URL), which looks like:

http://www.thewebsite.com?ID= U2FsdGVkX18ACGX1WK75GN5Idh gzp8Ajw/ qZJtnHk8dnEKH9DL4QcJsJtyThyK6QzDerhaNGeabn-6nPoym9kFU2TZ2 f4ke6QktelNe4/ Cr10kcZFZWbDYJRMuWODad9o. The URL, including the encrypted code, is then encoded as the security token 836.

FIG. 6 shows an example of a QR code generated by the software platform. This encoded QR code is printed onto a hospital identity card, insurance carrier card, wrist band, smartphone application, or any other tagging mechanism typically used in health care environment. Multiple different identifications 848, 948 in mobile health (Nike ID, Fitbit ID, diabetes ID), patient records (Hospital ID, Lab ID, Clinic ID, Rx ID), or personal records (Credit card, passport ID) may be linked to the encrypted security token using the linking engine 840, 940 and stored in the linking database 844, 944.

The embodiments disclosed herein are implemented as the software of an application program tangibly embodied on a program storage unit or tangible computer readable medium consisting of parts, or of certain mobile devices and/or a combination of devices. All or some of the servers maybe combined into one or more integrated servers.

All examples and conditional language recited herein are intended for educational purposes to aid the reader in understanding the principles of the invention and the concepts contributed by the inventor to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents hereof. Additionally, it is intended that such equivalents include both currently known equivalents as well as equivalents developed in the future, i.e., any elements developed that perform the same function, regardless of structure.

The invention claimed is:

1. A method for generating an encrypted identity of a user comprising said steps of:
   via a computer processor, generating a global identifier and query a database for a user, saving said global identifier with said user;
   via a computer processor, forming said encrypted identifier comprising:
   running an encryption algorithm, said running an encryption algorithm encrypts said global identifier via pairing with a stored server key;
   via a computer processor, forming a doubly encrypted identifier, said forming said doubly encrypted identifier comprising:
   running a second encryption algorithm, said running said second encryption algorithm encrypts said encrypted global identifier along with an encrypted date using an application key;
   via a computer processor, encoding a web site URL along with said doubly encrypted identifier into a QR code;
   printing said QR code on an output medium.

2. The method of claim 1, said output medium for said QR code selected from the group consisting of:
   an identity card;
   a medical identity card;
   a computer; and
   mobile device screen.

3. The method of claim 2, further comprising the steps of:
   via a processor, detecting a fraudulent activity of said QR code;
   deleting a compromised server key from said database.

4. The method of claim 2, further comprising:
   via a network interface, requesting input of a username and a password, said password corresponding to a value associated with said username in said database,
   via a processor, querying database for matching said username and said password; and granting access to said healthcare data if said match found.

5. A method of claim 2, further comprising the steps of:
   via a network interface, requesting said linked patient health information from other databases;
   Sending said matched patient health care information including linked health care information systems, Nike health and/or Fitbit information to said application.

6. The method of claim 1, further comprising the steps of:
   via a processor, storing in said database the links between said global unique identifier and health care identification data;
   said data selected from the group consisting of:
      hospital identification data;
      laboratory identification data;
      Nike identification data;
      insurance identification data;
      dental health plan identification data;
      prescription identification data;
      Fitbit identification data; and
      other health care identifications data.

7. The method of claim 1, further comprising the steps of:
   linking a manufacturing device using the Universal Device Identifier to the manufacturer ID, subcontractor ID, batch ID, customer id, and delivery date and received by person.

8. The method of claim 1, further comprising the steps of:
   linking a secure pharmacy pill container to a specified quantity of product.

9. The method of claim 1, further comprising said server key has a duration of time validity value stored in a database.

10. The system of claim 1, wherein said patient database contains identifiers to other hospital systems.

11. The system of claim 1, wherein said patient database contain links between said global unique identifier with health care identification data;
   said data selected from the group consisting of:
   hospital identification data;
   laboratory identification data;
   Nike identification data;
   insurance identification data;
   dental health plan identification data;
   prescription identification data; and
   Fitbit identification data.

12. A method for securely authenticating and authorizing the identity of a user comprising the steps of:
   via an image device, obtaining an image of a QR code and storing in a transient computer readable medium;
   via a computer processor, running a protocol, said protocol identifying if said QR code contains reference a website URL with a doubly encrypted identifier;
   via said computer processor, decrypting said doubly encrypted identifier and said application key into said encrypted global identifier;
   via computer network interface, sending a data message, said data message comprising said encrypted global identifier, said encrypted date, internet protocol address of the QR code reader, and said patient information request to the software system;
   via a server processor, querying a server key from the database for a server key matching said encrypted date;
   via a server processor, decrypting said encrypted global identifier;
   via a network interface, return requested data.

13. A system comprising:
   an image capture device comprising:
      a camera for reading an encrypted secure identifier encoded in a QR code;
      a QR code reader connected to a PC for reading an encrypted secure identifier encoded in said QR code;
      a processor for decrypting said encrypted secure identifier and a encrypted date and storing on a non-transient computer readable medium as a data packet;
   a server comprising:
      a server processor for receiving a data request from said image capture device, said data request comprising said decrypted secure identifier and an encrypted date, said server processor in response to receipt of said data request decrypting said data packet to a global identifier;
      a database stored on a non-transient computer readable medium, said database comprising:
      a server key registry;
         said server key registry searchable by said processor for returning a server key an effective date to match the encrypted date to use the server key to decrypted the encrypted secure identifier to global identifier;
      a patient registry database;
         said patient registry database searchable by said processor for returning patient data matching said global identifier.

* * * * *